(12) United States Patent
Shakespeare et al.

(10) Patent No.: US 12,005,227 B2
(45) Date of Patent: Jun. 11, 2024

(54) DIRECT DRUG/THERAPEUTIC INFUSION VIA TRANS-VASCULAR GLYMPHATIC SYSTEM AND METHOD

(71) Applicant: Product Realization Specialties, LLC, Macungie, PA (US)

(72) Inventors: W. Jeffrey Shakespeare, Macungie, PA (US); Jared B. Smith, Macungie, PA (US)

(73) Assignee: Product Realization Specialites, LLC, Macungie, PA (US)

( * ) Notice: Subject to any disclaimer, the term of this patent is extended or adjusted under 35 U.S.C. 154(b) by 263 days.

(21) Appl. No.: 17/494,917

(22) Filed: Oct. 6, 2021

(65) Prior Publication Data

US 2023/0109150 A1    Apr. 6, 2023

(51) Int. Cl.
| | | |
|---|---|---|
| *A61M 5/142* | (2006.01) | |
| *A61M 5/172* | (2006.01) | |
| *A61M 39/02* | (2006.01) | |

(52) U.S. Cl.
CPC ...... *A61M 5/14276* (2013.01); *A61M 5/1723* (2013.01); *A61M 2005/14284* (2013.01);
(Continued)

(58) Field of Classification Search
CPC ............ A61M 5/14276; A61M 5/1723; A61M 2005/14284; A61M 2005/1726;
(Continued)

(56) References Cited

U.S. PATENT DOCUMENTS

| | | | |
|---|---|---|---|
| 6,013,051 A | 1/2000 | Nelson | |
| 6,030,358 A | 2/2000 | Odland | |

(Continued)

FOREIGN PATENT DOCUMENTS

| | | |
|---|---|---|
| WO | 201928006 | 2/2019 |
| WO | 202041275 | 2/2020 |

OTHER PUBLICATIONS

Michael Churchill, 2021 Optimizations to Wireless Fiber Photometry and Wireless Optogenetics Products, Based on Customer Feedback.

(Continued)

*Primary Examiner* — Kai H Weng
*Assistant Examiner* — Nhu Q. Tran
(74) *Attorney, Agent, or Firm* — The Petruzzi Law Firm; James D. Petruzzi

(57) ABSTRACT

A dopamine or drug/therapeutics delivery and monitoring system for treatment of brain disease having an implantable titrator connected to the brain, a microtube for delivery of dopamine, a second microtube for withdrawal of CSF, a micropump for controlled pumping of dopamine into the brain responsive to sensed dopamine levels in the withdrawn CSF and a mixing chamber in the implantable titrator to combine withdrawn CSF with dopamine from a reservoir in the titrator to form a mixture for controlled delivery of the mixture. The system may have a fiber optic implanted and dopamine sensor responsive to certain sensed wavelengths of light received by a microcontroller. The system further has a dopamine reservoir and a carbon fiber resistance probe and may use fast scan cyclic voltammetry. A needle memory alloy having a straight and curved phase can be deployed into a blood vessel of a vascular system for trans-vascular delivery.

20 Claims, 7 Drawing Sheets

(52) U.S. Cl.
CPC .............. *A61M 2005/1726* (2013.01); *A61M 2039/025* (2013.01); *A61M 2202/0464* (2013.01); *A61M 2205/0266* (2013.01); *A61M 2205/3306* (2013.01); *A61M 2205/50* (2013.01); *A61M 2210/0693* (2013.01); *A61M 2210/12* (2013.01)

(58) Field of Classification Search
CPC .. A61M 2202/0464; A61M 2205/0266; A61M 2205/3306; A61M 2205/50; A61M 2210/0693; A61M 2210/12
See application file for complete search history.

(56) References Cited

U.S. PATENT DOCUMENTS

| | | | |
|---|---|---|---|
| 6,283,951 | B1* | 9/2001 | Flaherty ........... A61B 17/12109 604/164.11 |
| 6,782,292 | B2 | 8/2004 | Whitehurst |
| 6,950,707 | B2 | 9/2005 | Whitehurst |
| 7,684,867 | B2 | 3/2010 | Jaax et al. |
| 8,473,060 | B2 | 6/2013 | Leiter et al. |
| 8,945,448 | B2 | 2/2015 | Rinderknecht et al. |
| 8,946,151 | B2 | 2/2015 | Gill et al. |
| 10,258,284 | B1 | 4/2019 | Malek et al. |
| 10,258,487 | B2 | 4/2019 | Fulkerson et al. |
| 10,709,879 | B2 | 7/2020 | Iskandar et al. |
| 2003/0171711 | A1* | 9/2003 | Rohr ................... A61M 5/1723 604/67 |
| 2003/0171738 | A1* | 9/2003 | Konieczynski ... A61M 5/14276 604/500 |
| 2008/0312600 | A1* | 12/2008 | Krulevitch ........... A61M 5/158 604/181 |
| 2012/0238835 | A1 | 9/2012 | Hyde et al. |
| 2014/0288667 | A1* | 9/2014 | Oxley ................ A61N 1/36067 607/45 |
| 2018/0264191 | A1 | 9/2018 | Dagdeviren et al. |
| 2020/0138296 | A1* | 5/2020 | Pisanello ............. A61B 5/0075 |
| 2020/0281488 | A1* | 9/2020 | Kang ....................... A61B 5/24 |
| 2021/0052866 | A1* | 2/2021 | Roberts ................ A61M 27/006 |
| 2022/0111212 | A1* | 4/2022 | Howard .............. A61N 5/0622 |
| 2022/0202486 | A1* | 6/2022 | Morales .............. A61B 5/6853 |
| 2022/0313890 | A1* | 10/2022 | Riccardi ................. A61M 1/16 |

OTHER PUBLICATIONS

Neuronline, Understanding the Glymphatic System.
Miller et al "Stereotactic bony trajectory preservation for responsive neurostimulator lead placement following depth EEG recording."Cureus8, No. 3 (2016).
Mirza et al "Closed-Loop Implantable Therapeutic Neuromodulation Systems Based on Neurochemical Monitoring."Frontiers in Neuroscience 13 (2019): 808.

\* cited by examiner

DIRECT DRUG/THERAPEUTIC INFUSION VIA TRANS-VASCULAR GLYMPHATIC SYSTEM AND METHOD

CROSS REFERENCE TO RELATED APPLICATIONS

Not Applicable.

BACKGROUND OF THE INVENTION

The invention is a system for delivery of dopamine or other therapeutics to specific locations in the brain to treat Parkinson's disease or other neurological disorders through a micro-electomechanical system (MEMS) to control and manipulate small fluid volumes into and out of the brain.

Previous inventions were highly invasive (through skull and brain) for inserting microtubes into the brain and difficult to get proper placement to distribute the dopamine to affected areas. Doctors were not sure of the ability for the dopamine to diffuse into target areas through the Cerebral Spinal Fluid (CSF) after delivery to a ventricle, nor was the delivery specific to the target region of the putamen, instead diffusing throughout the brain leading to off-target effects. Furthermore, it was difficult to position the CSF sampling microtube and the fiber optic probe for accurate dopamine sampling and fiber photometry.

BRIEF SUMMARY OF THE INVENTION

A primary advantage of the invention is to provide for the controlled delivery of medication to the perivascular region of the brain.

Another advantage of the invention is to provide aid in delivering medication for cardiovascular, cancer or other neurological conditions via a microtube and specialized trans-vascular drug delivery system that penetrate the artery wall.

Yet another advantage of the invention is to provide dopamine or other drugs/therapeutics directly to the glymphatic system (perivascular region) which will deliver and distribute it focally to the Parkinson's affected brain regions in order to limit off-target adverse effects such as impulse-control disorder.

Still yet another advantage of the invention is to provide a microtube and MEMS pump implant that can be used to realize direct drug therapy with minimal, if any, invasive trauma to the brain.

Yet another advantage of the invention is to utilize specialized trans-vascular drug delivery system technology to sample CSF for Fast Scan Cyclic Voltammetry to measure dopamine concentration in the CSF for feedback control.

Yet another advantage of the invention is to utilize an implanted fiber to penetrate the arterial or venous wall and do fiber photometry in the brain parenchyma or the perivascular region/glymphatic system for feedback control of the implanted dopamine MEMS pump.

Yet another advantage of the invention is focal distribution of dopamine with feedback control which avoids the dyskinesia associated with systemic bolus administrations of Levodopa.

In accordance with a preferred embodiment of the present invention, there is shown a dopamine or other drug/therapeutics delivery and monitoring system for treatment of brain disease having an implantable titrator operatively connected to one or more selected regions of the brain, at least one microtube connected to the titrator for delivery of dopamine into the one or more selected regions of the brain, a second microtube operably connected to the titrator for withdrawal of CSF from the one or more regions of the brain, a micropump for controlled pumping of dopamine into the one or more regions of the brain responsive to dopamine levels in the withdrawn CSF in the region of the brain that are monitored by a dopamine sensor in the implantable titrator, and a mixing chamber in the implantable titrator to combine withdrawn CSF with dopamine from a reservoir in the titrator to form a mixture for controlled delivery of the mixture into the brain region.

In accordance with another preferred embodiment of the present invention, there is shown a dopamine or other drug/therapeutics delivery and monitoring system for treatment of brain disease having an implantable titrator operatively connected to one or more selected regions of the brain, at least one microtube comprising a needle of a memory alloy having a straight and curved phase which can be deployed into a blood vessel of a vascular system connected to the titrator for delivery of dopamine or other drug/therapeutics through the vessel wall into the glymphatic system and thence into the one or more selected regions of the brain, a second microtube operably connected to the titrator for withdrawal of CSF from the one or more regions of the brain, a micropump for controlled pumping of dopamine into the one or more regions of the brain responsive to dopamine levels in the withdrawn CSF in the region of the brain that are monitored by a dopamine sensor in the implantable titrator, a mixing chamber in the implantable titrator to combine withdrawn CSF with dopamine from a reservoir in the titrator to form a mixture for controlled delivery of the mixture into the brain region; and a fiber optic implanted into the brain region for sensing dopamine levels.

In accordance with another preferred embodiment of the present invention, there is shown a dopamine delivery and monitoring system for treatment of brain disease having an implantable titrator in a human operatively connected to one or more selected regions of the brain, at least one microtube connected to the titrator for delivery of dopamine into the one or more selected regions of the brain, a second microtube operably connected to the titrator for withdrawal through a microtube of CSF from the one or more regions of the brain, a micropump for controlled pumping of dopamine into the one or more regions of the brain responsive to dopamine levels in the withdrawn CSF in the region of the brain that are monitored by a dopamine sensor in the implantable titrator, a reservoir for storage of dopamine in the titrator, and a mixing chamber in the implantable titrator to combine withdrawn CSF with dopamine from the reservoir in the titrator to form a mixture for controlled delivery of the mixture into the brain region.

Other objects and advantages will become apparent from the following descriptions, taken in connection with the accompanying drawings, wherein, by way of illustration and example, preferred embodiments of the present invention are disclosed.

DETAILED DESCRIPTION OF THE PREFERRED EMBODIMENTS

Figure 1:
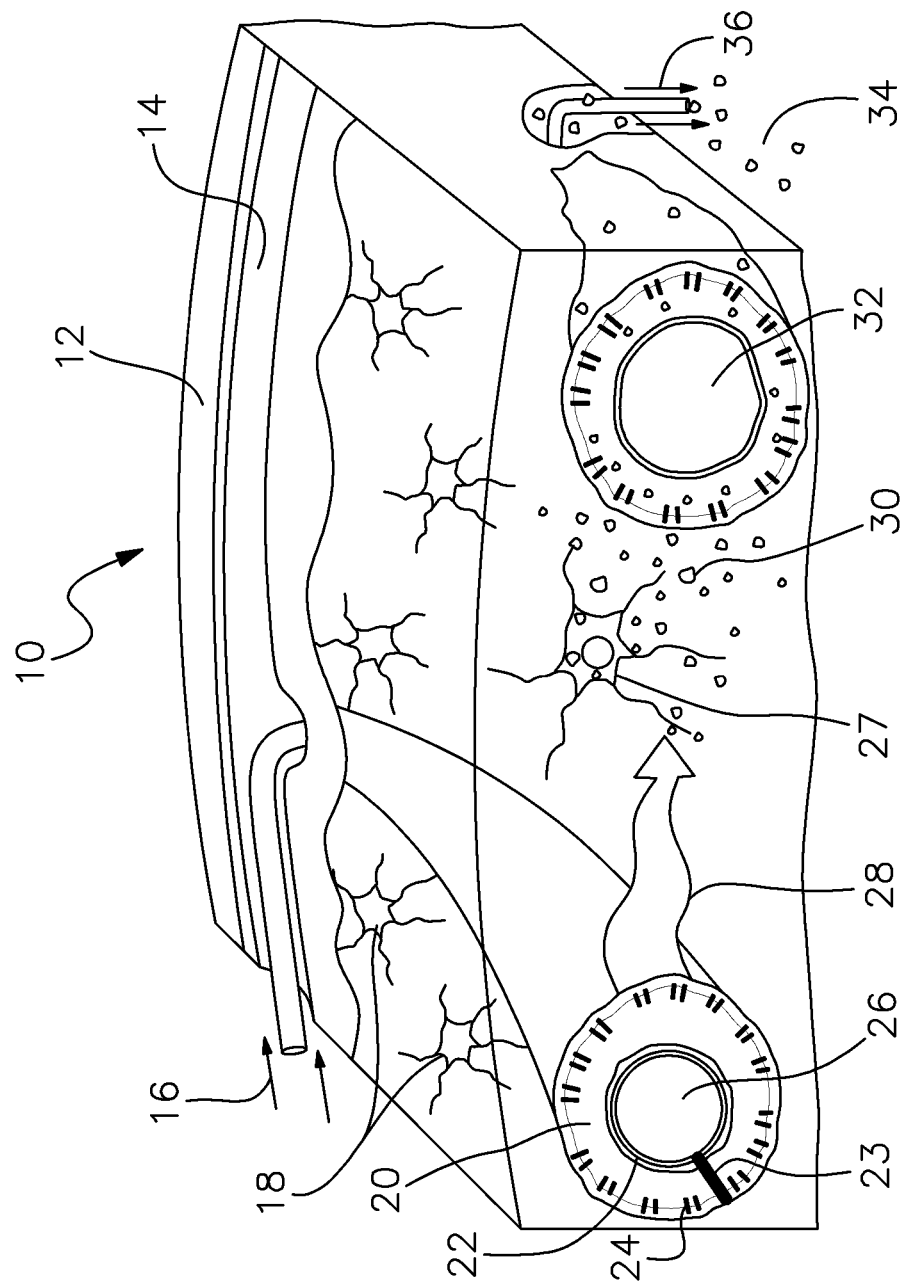
FIG. 1 is a diagram of the Glymphatic System and the delivery of Dopamine or other drugs through a structure penetrating the arterial or venous wall according to a preferred embodiment of the invention.

Detailed descriptions of the preferred embodiments are provided herein. It is to be understood, however, that the present invention may be embodied in various forms. Various aspects of the invention may be inverted, or changed in reference to specific part shape and detail, part location, or part composition. Therefore, specific details disclosed herein are not to be interpreted as limiting, but rather as a basis for the claims and as a representative basis for teaching one skilled in the art to employ the present invention in virtually any appropriately detailed system, structure or manner.

The drawings constitute a part of this specification and include exemplary embodiments to the invention, which may be embodied in various forms. It is to be understood that in some instances various aspects of the invention may be shown exaggerated or enlarged to facilitate an understanding of the invention.

The invention is a system for delivery of dopamine or other drugs to specific locations in the brain to treat Parkinson's disease or other diseases using feedback and sensing of dopamine levels in CSF from a region in the brain affected by disease such as Parkinson's (e.g. putamen). An implantable micropump using MEMS technology is connected via microtubes inserted in the brain via blood vessels for sampling Cerebrospinal fluid (CSF) on an ongoing basis. The use of a MEMS micropump allows precise drug delivery in nanoliters/hour to affected brain regions. A processor measures the dopamine concentration in the affected brain region with a sensor and adjusts the titration of dopamine delivered to that region to achieve the optimum dopamine concentration in the affected region as a closed loop control system, avoiding the blood-brain barrier constraint of current Levodopa therapies.

The system utilizes two independent dopamine concentration measurement methods. There are other methods such as G-protein-coupled receptor-activation-based DA (GRABDA) sensors.
a. Optical fluorescence method (e.g. dLight), including vector injection via cannula at time of implantation; and
b. Carbon fiber resistance method (fast scan cyclic voltammetry), including method of servicing carbon fiber.

Implantation of the device is aided by radiology (e.g. CT or MRI) to position the dopamine micro delivery tubes in the correct areas of the brain most in need of therapy. The subcutaneous dopamine reservoir may be refilled with a hypodermic needle without the need for surgery. A companion app for a smart phone that provides a readout of continuous dopamine levels in the affected region is also achievable.

A preferred embodiment of the present invention utilizes a structure that has been developed to minimize vascular occlusion while facilitating removal and replacement with minimal vascular trauma. This allows medication to be delivered to the perivascular region. It uses this specialized delivery structure technology to deliver dopamine or other therapeutics directly to the glymphatic system (perivascular region) which will deliver it to the Parkinson's affected brain regions (namely the putament via the lenticulostriatal arteries). This method of microtube and MEMS pump implant can be used to realize direct therapy with minimal, if any, invasive trauma to the brain.

The system and method utilize specialized delivery structure technology to sample CSF for Fast Scan Cyclic Voltammetry to measure dopamine concentration in the CSF for feedback control where the structure is modified with a cannula to penetrate the arterial or venous wall and sample CSF in the perivascular region/glymphatic system allowing feedback control of the implanted dopamine MEMS pump. Alternatively, the specialized delivery structure may be modified to include a fiber allowing fiber photometry to measure dopamine concentration in the CSF and regulate the MEMS pump in a closed loop system.

There are many advantages of the specialized Trans-Vascular/Drug/Therapeutic Delivery System. It eliminates brain trauma associated with microtube implant through the external brain regions, such as the cerebral cortex. It delivers dopamine focally to the affected areas. It utilizes the CSF pathways of the glymphatic system to distribute the dopamine more uniformly. It allows sampling of the local CSF dopamine concentration to maintain correct concentration, reducing side effects of dyskinesia. It has the potential for optical dopamine concentration measurement utilizing similar specialized Trans-Vascular Delivery System with a fiber through vascular wall technology. Properly localized dopamine delivery reduces side effects such as impulse control disorder.

Turning now to FIG. 1, there is shown a schematic diagram of the glymphatic system for carrying dopamine 10. Skull 12 surrounds subarachnoid space 14 through which perivascular cerebral spinal Fluid CSF influx 16 occurs. Neurons 18 are positioned throughout the brain and neuron 27 is shown more directly for illustrative purposes being acted upon by the preferred embodiment of the invention as more fully described herein. Para-arterial space 20 surrounds an artery 26 having artery wall 22. Aquaporin-4 protein 24, also known as AQP4, is a water channel protein encoded by the AQP4 gene in humans. AQP4 protein 24 belongs to the aquaporin family of integral membrane proteins that conduct water through the cell membrane. Convective flow 28 transports dopamine from a pump through Trans-Vascular delivery system 23 according to a preferred embodiment of the invention to neuron 27 affected by disease. Waste 30 produced by neuron 27 is then transported via vein 32 through para-venous efflux 36 to glymphatic system 34.

Figure 2:
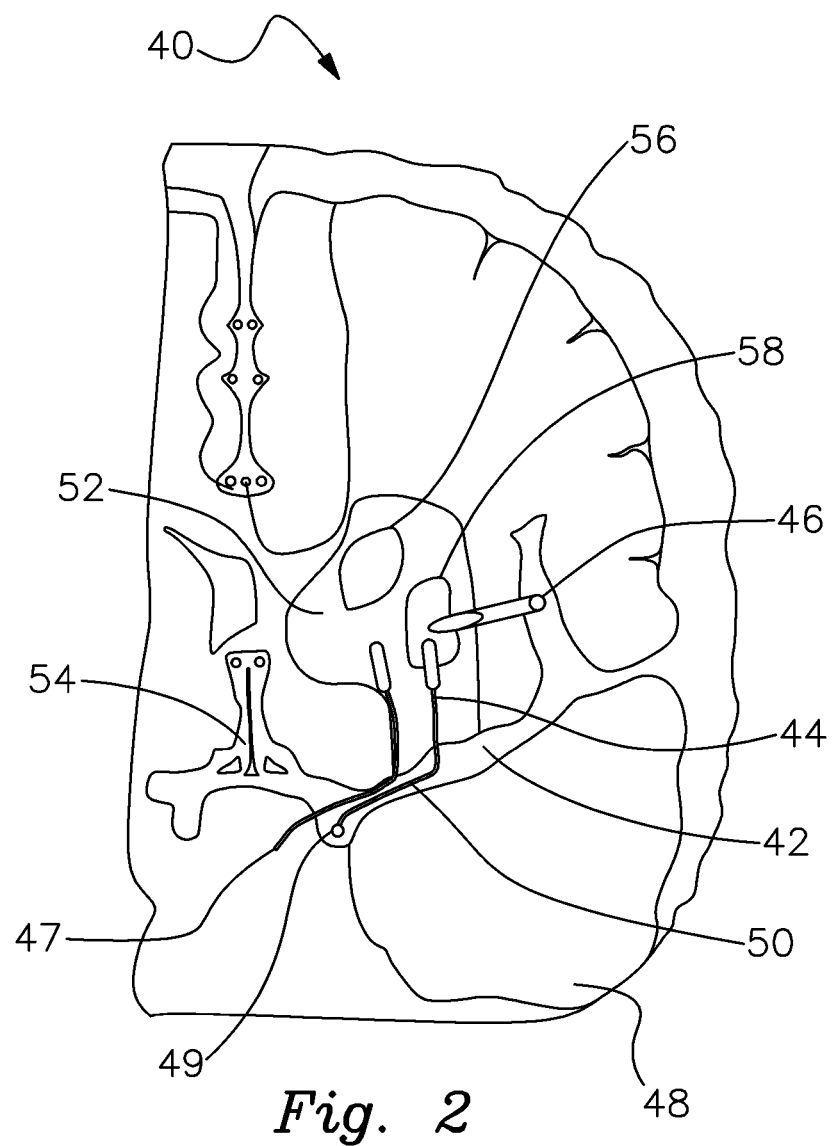
FIG. 2 is a diagram of a subject brain region and delivery tubes according to a preferred embodiment of the invention.

FIG. 2 shows a cross sectional view of brain hemisphere 40 having internal capsule 52 with putamen 58. Vascular microlumen 47 penetrates a vascular wall and withdraws a sample of CSF through the perivascular space, for measurement of dopamine concentration as further described below. Delivery microlumen 50 from a MEMS pump delivers dopamine or other drug through a vascular wall to the CSF surrounding the blood vessel in putamen 58. Internal carotid artery 49, temporal lobe 48 and middle cerebral artery 42 are shown with a drug delivery system and microlumen 50 emplaced through middle cerebral artery 42 for placement in putamen 58. Similarly, delivery may be accomplished through the venous system 46 into putamen 58. Microlumen 47 penetrates a vascular wall and withdraws a sample of CSF for dopamine concentration measurement discussed further below.

Dopamine is delivered through drug delivery system 44 through the vessel wall into the glymphatic system and diffuses to the local region of neurons affected by Parkinson's disease. By use of a Trans-Vascular drug delivery system along with a MEMS dopamine pump and measurement systems described further, allows a feedback control system to maintain proper dopamine levels in the locally affected regions of the brain. The system further minimizes brain trauma through the use of a small lumen and single emplacement rather than repeated intrusions into the brain tissue.

Figure 3A:
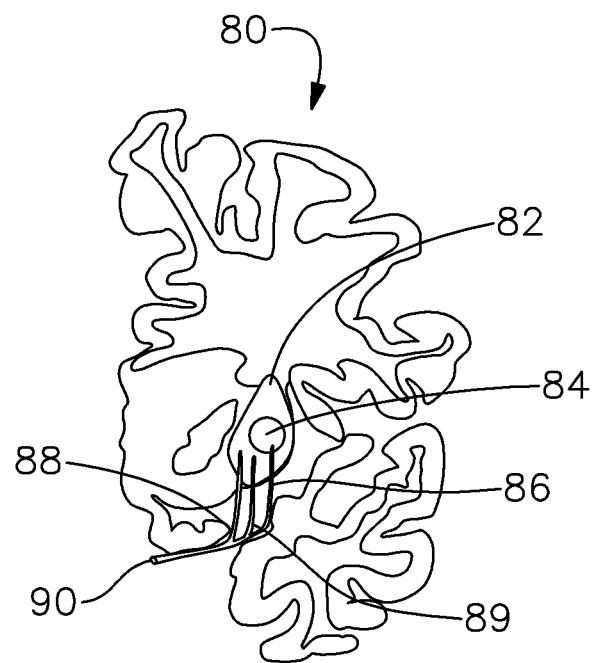
FIG. 3A is schematic cutaway section of the brain showing the putamen and probes according to a preferred embodiment of the invention.
Figure 3B:
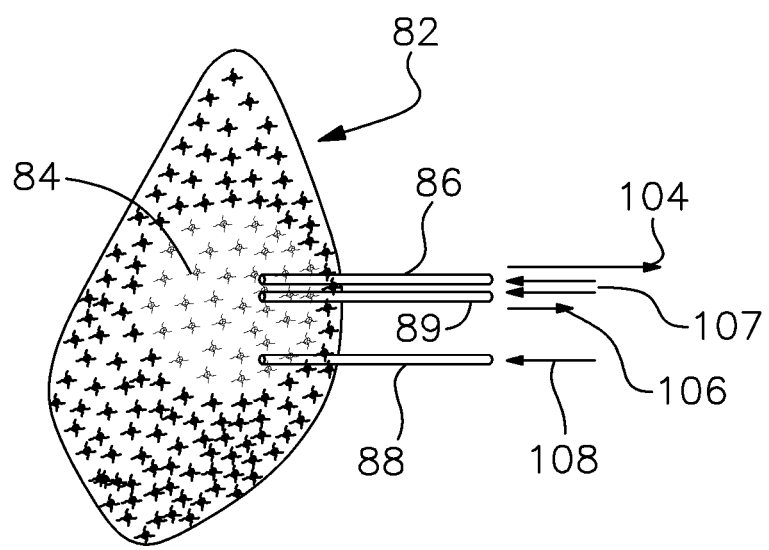
FIG. 3B is a drawing illustrating the putamen and probe according to a preferred embodiment of the invention including tubes to deliver dopamine and sample CSF for Fast Scan Cyclic Voltametry (FSCV) according to a preferred embodiment of the invention.

FIG. 3A shows a cross sectional diagram of affected brain portion 80 with middle cerebral artery 90 through which fluidic-μ Tube 88 for dopamine infusion and fluidic-μ Tube for CSF sample 89 and a fiber optic probe 86 also shown in FIG. 3B is taken through region 84 of putamen 82. FIG. 3B shows a blown-up view of putamen 82 having region 84 through which fiber optic probe 86 is emplaced for fiber photometry and fluidic-μ tube for CSF sample 89 in flow direction 106 for FSCV and Fluidic-μ Tube 88 for dopamine infusion in flow direction 108. Carbon fiber resistance (fast scan cyclic voltammetry), including methods of servicing carbon fiber may be used. Fiber optic probe 86 permits excitation wavelengths of light to be introduced 107 optionally at 405 nm @ 200 Hz and 470 nm @ 500 Hz with emissions 104 at 530 nm (deconvolved) to measure dopamine concentration using Fast Scan Cyclic Voltametry (FSCV). Optical fluorescence method (dLight), including vector injection during surgery may also be employed.

Using feedback control of the implanted dopamine MEMS pump, the Trans-Vascular drug delivery system technology is also used to sample CSF for Fast Scan Cyclic Voltammetry to measure dopamine concentration in the CSF and/or is modified with an implanted fiber to penetrate the arterial wall and perform fiber photometry in the perivascular region/glymphatic system using Optical fluorescence method (dLight) (fiber photometry), including vector injection using cannula; and Carbon fiber resistance method (fast scan cyclic voltammetry).

A processor measures the dopamine concentration in the affected brain region (in a sample of CSF) and adjusts the titration of dopamine delivered to that region to achieve the optimum dopamine concentration in the affected region as a closed loop control system, avoiding the blood-brain barrier constraint of current Levodopa therapies.

Implantation of the device is guided by radiology (e.g. CT/MRI) to position the dopamine micro delivery tubes in the correct areas of the brain most in need of therapy. The subcutaneous dopamine reservoir may be refilled with a hypodermic needle without the need for surgery. A companion app for a smart phone that provides a readout of continuous dopamine levels in the affected region is also contemplated.

Figure 4A:
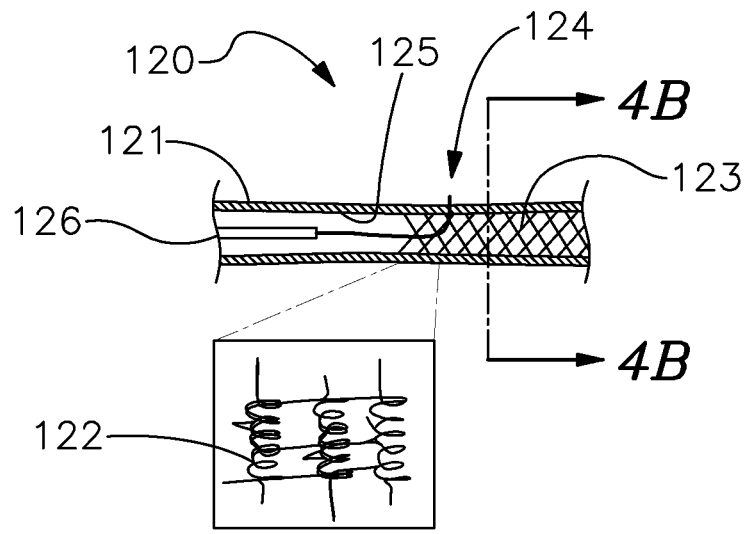
FIG. 4A is a drawing of a fiber optic and structure for fiber photometry dopamine concentration measurement according to a preferred embodiment of the invention.
Figure 4B:
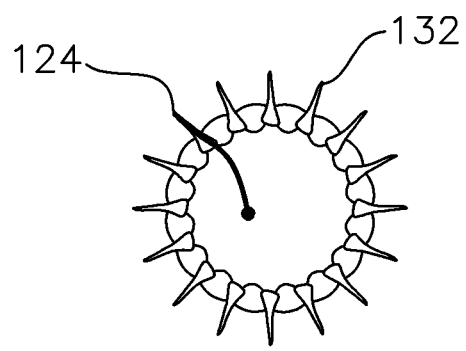
FIG. 4B is a cross sectional view of FIG. 4A showing the fiber optic and Trans-Vascular structure according to a preferred embodiment of the invention.

FIGS. 4A and 4B shows a Trans-Vascular drug delivery system for emplacement of a probe to be utilized according to a preferred embodiment of the invention. FIG. 4A shows infusion region 120 with microtube 126 and artery 121 having a fiber optic line 124 routed through deployed drug delivery system 122 through artery 121 to the perivascular region of interest. FIG. 4B is cross-sectional view of a portion of vein or artery 121 showing Trans-Vascular drug delivery system with fiber optic line 124 protruding through vessel wall into perivascular region to engage the perivascular/glymphatic space to measure dopamine in the CSF.

Figure 5A:
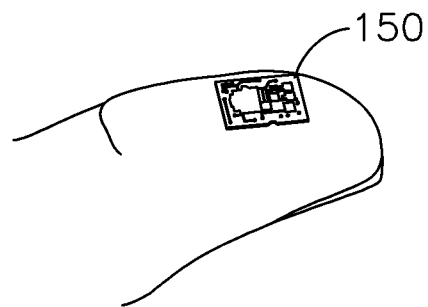
FIG. 5A shows an example of implantation microchip according to a preferred embodiment of the invention.
Figure 5B:
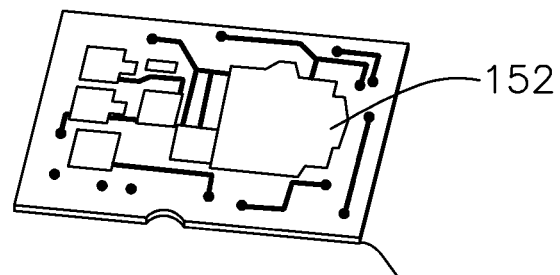
FIG. 5B shows a MEMS chip mounted on a ceramic substrate according to a preferred embodiment of the invention.
Figure 5C:
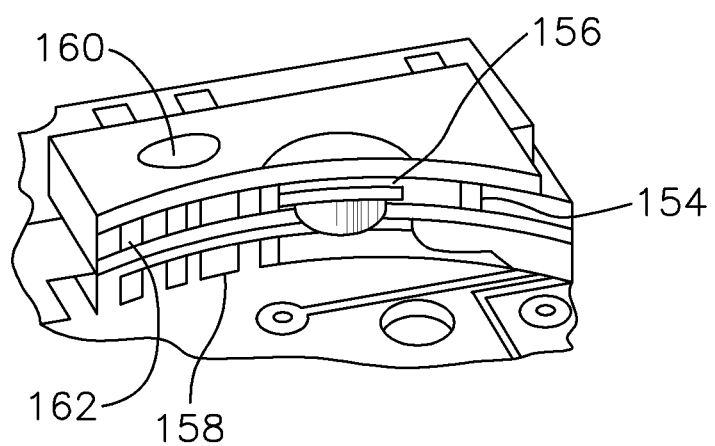
FIG. 5C shows a cross-section of a MEMS chip according to a preferred embodiment of the invention.

FIGS. 5A, B and C show a MEMS chip 152 mounted on a ceramic substrate 150 to form part of the micropump. An implantable micropump using MEMS technology is connected via microtubes inserted in the brain for sampling cerebrospinal fluid (CSF) on an ongoing basis. FIG. 5C shows a cross-section of a MEMS chip showing an inlet valve 154, a pumping chamber 156, a first detector 158 and second detector 160 and an outlet valve 162. The MEMS pump is in fluid communication with a CSF reservoir through a mixing valve shown in FIG. 6 that receives a CSF sample from the affected area, is controlled by a microcontroller to provide the appropriate amount of dopamine from the reservoir in response to sensors monitoring the dopamine in the CSF.

Figure 6:
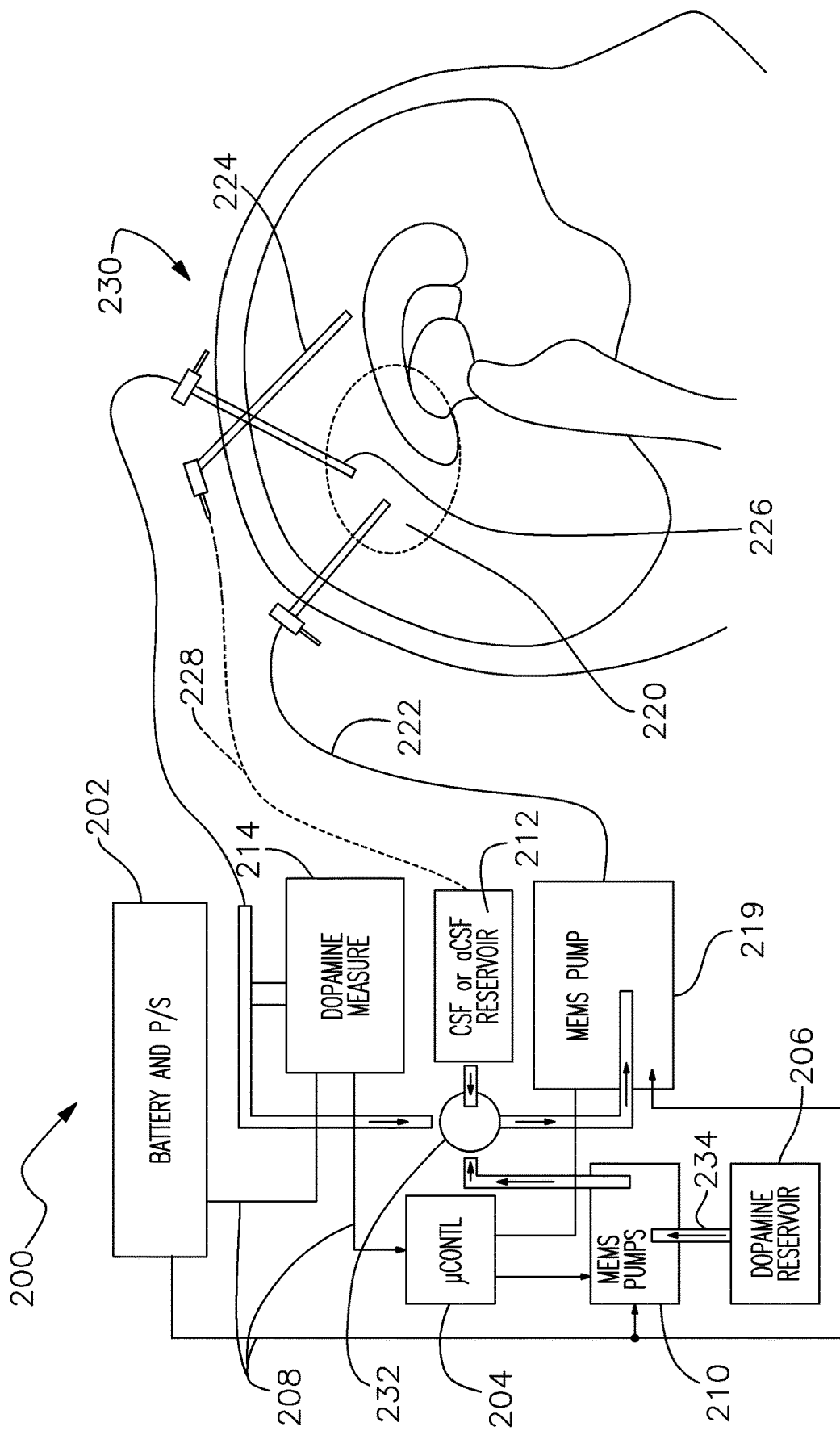
FIG. 6 shows a block diagram of the method of delivery of dopamine to a brain region according to a preferred embodiment of the invention.

FIG. 6 shows an implantable dopamine titrator 200, having a battery and power supply 202 with power and electronic control lines 208, microcontroller 204 electrically connected to MEMS micropumps 210 and 219, dopamine reservoir 206 operably connected to MEMS PUMP 210, CSF reservoir 212 operably connected to mixing valve 232, and dopamine measure sensor 214 operably connected to a patient's brain region 220 through microtube 226. Implantable dopamine titrator 200 is connected via several microtubes into the affected brain region 220 of subject 230. Pump microtube 222 is implanted into brain region 220 for delivery of dopamine as further described below. CSF sample microtube 226 is implanted into brain region 220 for continuous sampling of CSF in brain region 220. Microtube 224 may optionally have optical fiber 228 implanted in the brain for sensing of dopamine near brain region 220. Microtubes 222, 224 and 226 are inserted using stereo-tactical methods well known in the art.

Figure 7A:
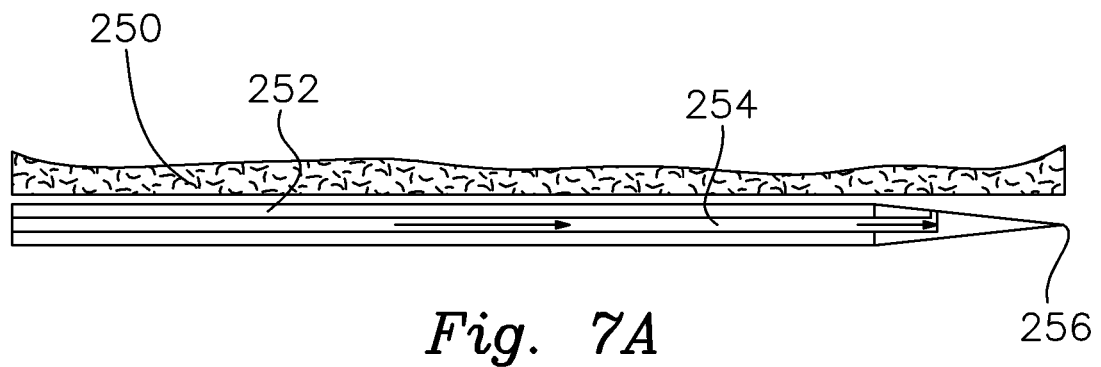
FIGS. 7A and 7B show a specialized Trans-Vascular drug/therapeutic delivery system according to a preferred embodiment of the invention.
Figure 7B:
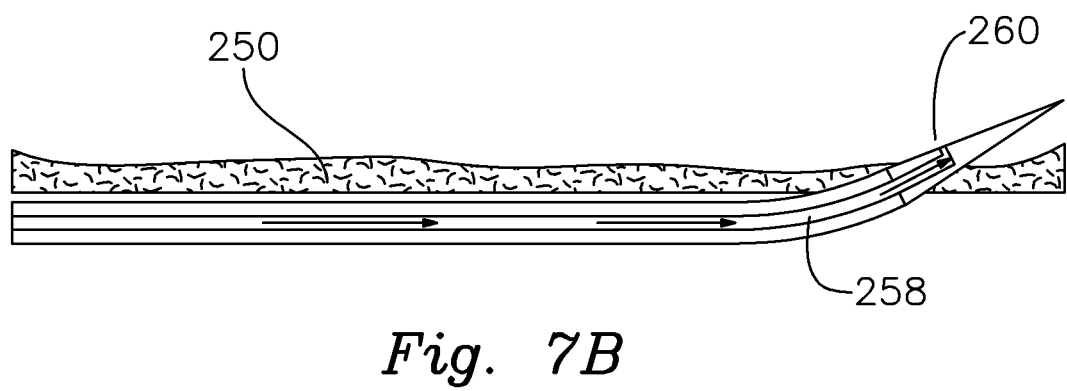

FIGS. 7A and 7B show a Trans-Vascular drug delivery system having microtube 252 made of nitinol or other shape memory alloy with internal lumen 254 with hypodermic style needle end 256 designed to penetrate vessel wall 250 for CSF sampling, drug delivery or fiber optic deployment. When the correct position is achieved, the tube is heated via Joule heating and the straight Martensite phase delivery tube is transitioned to Austenite causing the tube to curve and penetrate the blood vessel wall with flow of drug delivery 258 through port 260. The OD of the shape memory alloy tube is expected to be in the 10 um to 20 um range. This concept reduces the cross-sectional area occluded by the tube so that the delivery system can be deployed into smaller blood vessel and allows the delivery system to be withdrawn and replaced as needed. One preferred method of constructing such a tube is to extrude a tube of several millimeters diameter and then by means of heating and stretching the tube in a suitable fixture, cause the OD and ID to reduce to the operative diameters similar to the method of drawing optical fiber.

Operation of implantable dopamine titrator 200 is accomplished by continuous operation of MEMS micropumps 210 and 219 to allow precise drug delivery in nanoliters/hour to affected brain region 220. Microcontroller 204 measures the dopamine concentration in brain region 220 in a sample of CSF drawn from microtube 226 through dopamine measure sensor 214 and adjusts the titration of dopamine delivered to that region to achieve the optimum dopamine concentration in the affected region as a closed loop control system, avoiding the blood-brain barrier constraint of current Levodopa therapies. Dopamine reservoir 206 provides dopamine through channel 234 through MEMS micropump 210 to mixing valve 232 that combines CSF from microtube 226 and CSF from CSF reservoir 212 with dopamine from dopamine reservoir 206 in the appropriate amount to be delivered via MEMS micropump 219 back into brain region 220 via microtube 222. Optionally, microtube 224 having optical fiber 228 imparts excitation wavelengths of light as previously described which data is then transmitted back to implantable dopamine titrator 200 for processing by microcontroller 204 using fiber photometry.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the issued claims.

We claim:

1. A dopamine or other drug/therapeutics delivery and monitoring system for treatment of brain disease comprising:
   a. an implantable titrator operatively connected to one or more selected regions of the brain via the glymphatic system and further comprising:
      a micropump for controlled pumping of dopamine or other drug into the one or more regions of the brain responsive to dopamine levels in the withdrawn CSF in the region of the brain that are monitored by a dopamine sensor; and
      a mixing chamber to combine withdrawn CSF with dopamine or other drug from a reservoir in the titrator to form a mixture for controlled delivery of the mixture into the brain region via the glymphatic system;
   b. at least one microtube connected to the titrator for delivery of dopamine or other drug into the one or more selected regions of the brain wherein the microtube is inserted through an arterial wall for delivery of the dopamine or other drug into the one or more regions of the brain, allowing the glymphatic system to effectively distribute the dopamine or other drug/therapeutic to the necessary regions of the brain requiring therapy; and
   c. a second microtube operably connected to the titrator for withdrawal of CSF from the one or more regions of the brain glymphatic system.

2. The dopamine or other drug/therapeutics delivery and monitoring system for treatment of brain disease of claim 1 further comprising a fiber optic implanted into the brain region via the elymphatic system.

3. The dopamine or other drug/therapeutics delivery and monitoring system for treatment of brain disease of claim 1 wherein the dopamine sensor is responsive to certain sensed wavelengths of light received by a microcontroller in the titrator.

4. The dopamine or other drug/therapeutics delivery and monitoring system for treatment of brain disease of claim 1 further comprising a microcontroller operably connected to the MEMS pump and dopamine sensor.

5. The dopamine or other drug/therapeutics delivery and monitoring system for treatment of brain disease of claim 1 further comprising a specialized Trans-Vascular drug/therapeutic delivery system operatively connected to the micropump configured for delivery of dopamine or other drug/therapeutics through the arterial wall into the one or more regions of the brain, and configured to allow a glymphatic system to effectively distribute the dopamine or other drug/therapeutic to the necessary regions of the brain requiring therapy.

6. The dopamine or other drug/therapeutics delivery and monitoring system for treatment of brain disease of claim 1 further comprising the dopamine reservoir operably connected to the micropump.

7. The dopamine or other drug/therapeutics delivery and monitoring system for treatment of brain disease of claim 1 further comprising using fast scan cyclic voltammetry with a carbon fiber resistance probe.

8. The dopamine or other drug/therapeutics delivery and monitoring system for treatment of brain disease of claim 1 further comprising a mixing valve.

9. The dopamine or other drug/therapeutics delivery and monitoring system for treatment of brain disease of claim 1 further comprising a needle of a memory alloy having a straight and curved phase which can be deployed into the arterial blood vessel of a vascular system designed to penetrate the vessel wall and deliver dopamine or other drug/therapeutic into the glymphatic system effectively bypassing the blood brain barrier.

10. he dopamine or other drug/therapeutics delivery and monitoring system for treatment of brain disease of claim 9 further comprising a fiber optic for fiber photometry.

11. A dopamine or other drug/therapeutics delivery and monitoring system for treatment of brain disease comprising:
   a. an implantable titrator operatively connected to one or more selected regions of the brain via the glymphatic system comprising:
      a micropump for controlled pumping of dopamine into the one or more regions of the brain responsive to dopamine levels in the withdrawn CSF in the region of the brain that are monitored by a dopamine sensor in the implantable titrator; and
      a mixing chamber in the implantable titrator to combine withdrawn CSF with dopamine from a reservoir in the titrator to form a mixture for controlled delivery of the mixture into the brain region;
   b. at least one microtube comprising a needle of a memory alloy having a straight and curved phase deployed through an arterial blood vessel of a vascular system connected to the titrator configured for delivery of dopamine or other drug/therapeutics through the vessel wall into the glymphatic system and thence into the one or more selected regions of the brain;
   c. a second microtube operably connected to the titrator for withdrawal of CSF from the one or more regions of the elymphatic system; and
   d. a fiber optic implanted into the brain region for sensing dopamine levels in the elymphatic system.

12. The dopamine or other drug/therapeutics delivery and monitoring system for treatment of brain disease of claim 11 further comprising the needle of a memory alloy having a straight and curved phase which can be deployed into the arterial blood vessel of a vascular system for withdrawal of CSF from the one or more regions of the brain via the elymphatic system.

13. The dopamine or other drug/therapeutics delivery and monitoring system for treatment of brain disease of claim 11 further using Fast Scan Cyclic Voltammetry.

14. The dopamine or other drug/therapeutics delivery and monitoring system for treatment of brain disease of claim 11 further comprising a microcontroller to provide the appropriate amount of dopamine from the reservoir in response to the sensor monitoring the dopamine in the CSF of the glymphatic system.

15. The dopamine or other drug/therapeutics delivery and monitoring system for treatment of brain disease of claim 11 further comprising optical fluorescence using excitation wavelengths of light.

16. A dopamine delivery and monitoring system for treatment of brain disease comprising:
   a. an implantable titrator in a human operatively connected to one or more selected regions of the brain via the glymphatic system and further comprising;
      a micropump for controlled pumping of dopamine into the one or more regions of the brain responsive to dopamine levels in the withdrawn CSF in the region of the brain that are monitored by a dopamine sensor in the implantable titrator;
      a reservoir for storage of dopamine in the implantable titrator; and
      a mixing chamber in the implantable titrator to combine withdrawn CSF with dopamine from the reservoir in the titrator to form a mixture for controlled delivery of the mixture into the brain region via the glymphatic system;
   b. at least one microtube connected to the titrator for delivery of dopamine through a cerebral artery for diffusion to one or more selected regions of the brain via the glymphatic system; and
   c. a second microtube operably connected to the titrator for withdrawal through a microtube of CSF from the one or more regions of the glymphatic system in the brain.

17. The dopamine delivery and monitoring system for treatment of brain disease of claim 16 wherein the micropump is a MEMS pump.

18. The dopamine delivery and monitoring system for treatment of brain disease of claim 16 further comprising an optical fiber that imparts excitation wavelengths of light.

19. The dopamine delivery and monitoring system for treatment of brain disease of claim 17 wherein the MEMS pump is in fluid communication with the reservoir through a mixing valve.

20. The dopamine delivery and monitoring system for treatment of brain disease of claim 16 further comprising a battery and power supply.

* * * * *